United States Patent [19]

Seido et al.

[11] Patent Number: 4,994,602
[45] Date of Patent: Feb. 19, 1991

[54] PROCESS FOR PREPARING OPTICALLY ACTIVE 6-T-BUTYOXY-3,5-DIHYDROXYHEXANOIC ESTERS

[75] Inventors: Nobuo Seido; Noboru Sayo; Hidenori Kumobayashi, all of Kanagawa, Japan

[73] Assignee: Takasago International Corporation, Tokyo, Japan

[21] Appl. No.: 485,692

[22] Filed: Feb. 27, 1990

[30] Foreign Application Priority Data

Feb. 27, 1989 [JP] Japan .................................. 1-43196

[51] Int. Cl.⁵ .............................................. C07C 69/66
[52] U.S. Cl. .................................................. 560/186
[58] Field of Search ......................................... 560/186

[56] References Cited

PUBLICATIONS

CA 91(15): 123310n, 1979.
CA 93(25): 238692x, 1980.
CA 108(7): 55601a, 1988.

Primary Examiner—Paul J. Killos
Attorney, Agent, or Firm—Sughrue, Mion, Zinn, Macpeak & Seas

[57] ABSTRACT

A process for preparing an optically active 6-t-butoxy-3,5-dihydroxyhexanoic ester represented by formula:

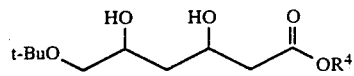

wherein t-Bu represents a t-butyl group; and $R^4$ represents a lower alkyl group, which is useful as a precursor of a lactone moiety of campactin, mevinolin or analogues thereof is disclosed, comprising asymmetrically hydrogenating a 4-t-butoxyacetoacetic ester in the presence of a ruthenium-optically active phosphine complex to obtain an optically active 4-t-butyoxy-3-hydroxybutanoic ester, reacting the ester with a lithium enolate of an acetic ester to obtain an optically active 6-t-butyoxy-5-hydroxy-3-oxohexanoic ester, and asymmetrically hydrogenating the resulting ester in the presence of a ruthenium-optically active phosphine complex as a catalyst. The desired product can be obtained in good yield at high stereoselectivity.

10 Claims, No Drawings

PROCESS FOR PREPARING OPTICALLY ACTIVE 6-T-BUTYOXY-3,5-DIHYDROXYHEXANOIC ESTERS

FIELD OF THE INVENTION

This invention relates to a process for preparing an optically active 6-t-butoxy-3,5-dihydroxyhexanoic ester useful as an intermediate of starting materials for synthesizing drugs.

BACKGROUND OF THE INVENTION 6-t-Butoxy-3,5-dihydroxyhexanoic esters in which the steric configurations at the 3- and 5-positions are (R)-configuration and (S)-configuration, respectively, are known to be easily converted to a lactone moiety of the chemical structures of compactin and mevinolin which are attracting attention as cholesterol reducing agents [cf. K. Prasad et al., *Tetrahedron Lett.*, Vol. 25, p. 3391 (1984)]. The lactone moiety stated above is assumed to be an active part of an inhibitor on 3-hydroxy-3-methylglutaryl-CoA reductase, one of the predominant enzymes regulating cholesterol biosynthesis, and a number of analogues having this lactone moiety have been synthesized [cf. J. R. Prous (ed.), *Drugs of the Future*, Vol. 12, No. 5, p. 437 (1987)].

Conventional processes applicable to synthesis of optically active 6-t-butoxy-3,5-dihydroxyhexanoic esters include a process for synthesizing an optically active 1,3-diol compound by making use of naturally occurring D-glucose as reported in T. Lee et al., *Tetrahedron Lett.*, Vol. 26, p. 4995 (1985) and Y. Yang et al., *Tetrahedron Lett.*, Vol. 23, p. 4305 (1982). Further, methods for constructing the two asymmetric carbon atoms one by one include a method comprising diastereo-selective reduction by using a trialkylboron as a specific reactant as described in K. Chen et al., *Tetrahedron Lett.*, Vol. 28, p. 155 (1987), a method comprising asymmetric aldol reaction as described in J. E. Lynch et al., *Tetrahedron Lett.*, Vol. 28, p. 138 (1987), a method of using asymmetric epoxidation as described in K. Prasad et al., *Tetrahedron Lett.*, Vol. 25, p. 3391 (1984), and a method of using a microorganism as described in P. R. Ortizo De Montellano et al., *J. Am. Chem. Soc.*, Vol. 98, p. 2018 (1976).

The process for obtaining an optically active 1,3-diol compound by using a naturally occurring substance is disadvantageous in that long reaction steps are required for obtaining the desired product. The processes starting with an optically active substance obtained by optical resolution are inevitably attended by production of an unnecessary enantiomer, giving rise to a problem of production efficiency. Further, in the processes using a microorganism, the steric configuration of the product is limited in many cases and, also, separation of the product from microbial cells is complicated.

A diastereoselective technique in which one asymmetric point is made use of to induce another asymmetry may be applied to synthesis of the 1,3-diol compound according to the present invention. However, such configurational control generally requires an expensive reagent.

SUMMARY OF THE INVENTION

One object of this invention is to provide a process for preparing an optically active 6-t-butoxy-3,5-dihydroxyhexanoic ester with industrial advantages.

As a result of extensive investigations, the inventors have found that the above object of this invention is accomplished by a process for advantageously preparing the desired 6-t-butoxy-3,5-dihydroxyhexanoic ester in high yield with stereoselectivity, which comprises (1) asymmetrically hydrogenating a 4-t-butoxyacetoacetic ester which is easily synthesized from diketene, in the presence of a ruthenium-optically active phosphine complex as a catalyst to obtain an optically active 4-t-butoxy-3-hydroxybutyric ester, (2) reacting the product with a lithium enolate of an acetic ester to obtain an optically active 6-t-butoxy-5-hydroxy-3-oxohexanoic ester, and (3) diastereoselectively hydrogenating the product using a ruthenium-optically active phosphine complex as a catalyst.

The present invention provides a process for preparing an optically active 6-t-butoxy-3,5-dihydroxyhexanoic ester represented by formula (VII):

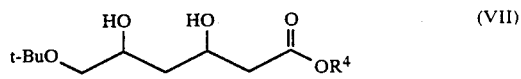

(VII)

wherein t-Bu represents a t-butyl group; and $R^4$ represents a lower alkyl group, comprising asymmetrically hydrogenating a 4-t-butoxyacetoacetic ester represented by formula (I):

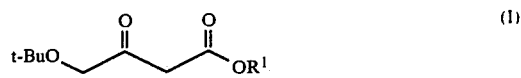

(I)

wherein t-Bu is as defined above; and $R^1$ represents a lower alkyl group, in the presence of a ruthenium-optically active phosphine complex represented by formula (II):

$$Ru(R^2\text{—BINAP})(O_2CR^3)_2 \quad \text{(II)}$$

wherein $R^2$-BINAP represents a tertiary phosphine represented by formula (III):

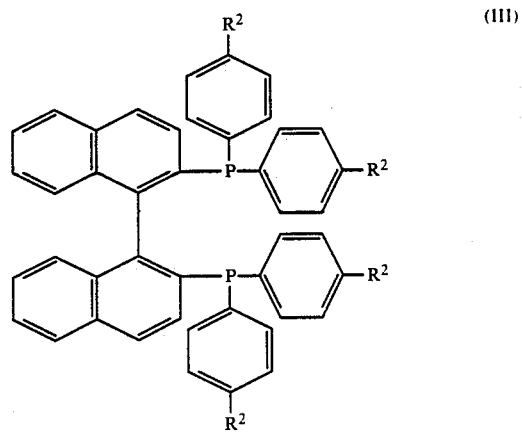

(III)

wherein $R^2$ represents a hydrogen atom or a methyl group; and $R^3$ represents a lower alkyl group or a trifluoromethyl group, to obtain an optically active 4-t-butoxy-3-hydroxybutanoic ester represented by formula (IV):

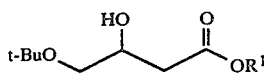 (IV)

wherein t-Bu and $R^1$ are as defined above, reacting the compound represented by formula (IV) with a lithium enolate of an acetic ester to obtain an optically active 6-t-butoxy-5-hydroxy-3-oxohexanoic ester represented by formula (V):

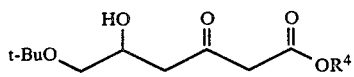 (V)

wherein t-Bu and $R^4$ are as defined above, and then subjecting the compound represented by formula (V) to asymmetric hydrogenation using a ruthenium-optically active phosphine complex represented by formula (VI):

 (VI)

wherein $R^2$-BINAP is as defined above; and Et represents an ethyl group, as a catalyst.

DETAILED DESCRIPTION OF THE INVENTION

The term "lower alkyl group" as referred to in the definition for the foregoing formulae preferably means an alkyl group containing from 1 to 4 carbon atoms.

The compound represented by formula (I) which is used as a starting material of the process according to the present invention, can be obtained from easily commercially available 4-chloroacetoacetic esters by the process described in D. Seebach et al., *Synthesis*, p. 37 (1986).

The ruthenium-optically active phosphine complex represented by formula (II) can be obtained by the process disclosed in JP-A-62-265293 (the term "JP-A" as used herein means an "unexamined published Japanese patent application"). In more detail, the complex of formula (II) wherein $R^3$ is a lower alkyl group can be prepared by reacting $Ru_2Cl_4(R^2-BINAP)_2(NEt_3)$ with a carboxylic acid salt in an alcohol solvent, e.g., methanol, ethanol, and t-butanol, removing the solvent from the reaction mixture by distillation, and extracting the residue from a solvent, e.g., diethyl ether and ethanol. The complex of formula (II) wherein $R^3$ is a trifluoromethyl group can be obtained by reacting the thus prepared complex $Ru(R^2-BINAP)(O_2CR^3)_2$ with trifluoroacetic acid in methylene chloride.

Specific examples of the ruthenium-optically active phosphine complex of formula (II) are shown below.

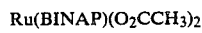

[wherein BINAP represents 2,2'-bis(diphenylphosphino)-1,1,'-binaphthyl]

[wherein Tol-BINAP represents 2,2,'-bis(di-p-tolylphosphino)-1,1,'-binaphthyl]

The ruthenium-optically active phosphine complex represented by formula (VI) can be obtained by the processes disclosed in T. Ikariya et al., *J. Chem. Soc., Chem. Commun.*, p. 922 (1985) and JP-A-61-63690. That is, it is prepared by reacting ruthenium chloride and cycloocta-1,5-diene (hereinafter abbreviated as COD) in ethanol to obtain $[RuCl_2(COD)]_n$ and then heating the resulting compound and $R^2$—BINAP in a solvent, e.g., toluene or ethanol, in the presence of triethylamine.

Specific examples of the ruthenium-optically active phosphine complex of formula (VI) are shown below.

Phosphine derivatives in the above-enumerated ruthenium-optically active phosphine complexes include the respective enantiomers, though not shown.

The present invention is carried out as follows. A 4-t-butoxyacetoacetic ester (I) is dissolved in an alcohol, e.g., methanol, ethanol, and isopropanol. A ruthenium-optically active phosphine complex (II) is added to the solution in an amount of from 0.001 to 0.1 mole, preferably from 0.002 to 0.01 mole, per mole of the substrate (I), and hydrogenation is conducted at a temperature of from 25° to 100° C. under a hydrogen pressure of from 5 to 150 kg/cm², preferably from 30 to 70 kg/cm² until the substrate is completely consumed to obtain an optically active 4-t-butoxy-3-hydroxybutanoic ester (IV). The ester (IV) is then reacted with a lithium enolate of an acetic ester prepared by the process described in T. E. Linth et al., *Tetrahedron Lett.*, Vol. 28, p. 1385 (1987) in tetrahydrofuran at a temperature of −50° C., and the reaction mixture is worked-up in a usual manner to obtain a 6-t-butoxy-5-hydroxy-3-oxohexanoic ester (V).

The resulting ester (V) is dissolved in an alcohol, e.g., methanol, ethanol, and isopropanol. To the solution is added a ruthenium-optically active phosphine complex (VI) in an amount of from 0.001 to 0.1 mole, preferably from 0.002 to 0.01 mole, per mole of the substrate (V), and hydrogenation is conducted at a temperature of from 5° to 100° C., preferably from 30° to 50° C., under a hydrogen pressure of from 10 to 120 kg/cm², preferably from 50 to 100 kg/cm². The solvent is removed by distillation, and the residue is purified by silica gel column chromatography to obtain the desired optically active 6-t-butoxy-3,5-dihydroxyhexanoic ester (VII).

The t-butyl group as a protective ether group in the starting ester (I) may be replaced with other protective groups, such as a benzyl group and a trialkylsilyl group. However, a t-butyl group is superior to other protective groups from the standpoint of providing the highest stability and the highest yield in the subsequent reaction.

In order to obtain an optically active syn-diol compound (VII) in the final stage (diastereoselective asymmetric hydrogenation), where the steric configuration of the 5-positioned carbon atom of the substrate (V) is an (S)-configuration, it is essential to combine ruthenium with (R)-BINAP; and where said steric configuration is an (R)-configuration, ruthenium should be combined with (S)-BINAP.

The present invention will now be illustrated in greater detail by way of Examples, but it should be understood that the present invention is not to be construed as being limited thereto. All the percents are by weight unless otherwise specified. Analyses of products obtained in these examples were performed by means of the following analytical instruments.

Gas Chromatography:
Chromatograph: Shimadzu GC-9A, manufactured by Shimadzu Corporation
Column: OV-101 silica capillary (diameter: 0.25 mm; length: 25 m), manufactured by Gasukuro Kogyo K. K.
Measurement Temp.: 100° to 250° C., at a rate of temperature rise of 10° C./min High-Performance Liquid Chromatography:
Chromatograph: Hitachi Liquid Chromatography L-6000, manufactured by Hitachi, Ltd.
Column: Develosil® 100-3 (diameter: 4.6 mm; height: 250 mm), manufactured by Nomura Kagaku K. K.
Developing Solvent: diethyl ether/hexane: 1/9 (by volume), at a flow rate of 1 ml/min
Detector: UV Detector L-4000 (UV 254 nm), manufactured by Hitachi, Ltd.

EXAMPLE 1

Preparation of Methyl (3S)-4-t-Butoxy-3-hydroxybutanoate

In a 100 ml-volume egg plant type flask equipped with a three-way cock whose atmosphere had been replaced with nitrogen was charged 90 mg (0.106 mmole) of Ru((R)-BINAP)(O$_2$CCH$_3$)$_2$, and 20 g (106 mmole) of methyl 4-t-butoxy-3-one-butanoate and 60 ml of methanol were added thereto to form a solution. The solution was transferred to a 200 ml-volume autoclave whose atmosphere had been displaced with nitrogen and stirred at 30° C. for 16 hours under a hydrogen pressure of 100 kg/cm$^2$ to conduct hydrogenation. The solvent was removed by distillation, and the residue was distilled under reduced pressure to obtain 21.1 g (yield: 100%) of methyl (3S)-4-t-butoxy-3-hydroxybutanoate as a colorless transparent substance.

Boiling Point: 78° C./2 mmHg
H-NMR δ ppm: 1.20 (s, 9H), 2.50 (d, J=7Hz, 2H), 3.31 (d, J=6Hz, 2H), 3.65 (s, 3H), 4.10 (m, 1H)

The methyl (3S)-4-t-butoxy-3-hydroxybutanoate thus obtained was reacted with (R)-(+)-α-methoxy-α-trifluoromethylphenylacetyl chloride to obtain an ester. On analysis by highperformance liquid chromatography (HPLC), the product was found to be a mixture comprising 98.2% of methyl (3S)-4-t-butoxy-3-hydroxybutanoate and 1.8% of methyl (3R)-4-t-butoxy-3-hydroxybutanoate, and the optical purity of the methyl (3S)-4-t-butoxy-3-hydroxybutanoate was 96.4 %ee.

EXAMPLE 2

Preparation of Methyl (3R)-4-t-Butoxy-3-hydroxybutanoate

In a 100 ml-volume egg plant type flask equipped with a three-way cock whose atmosphere had been displaced with nitrogen was charged 6.1 mg (0.066 mmole) of Ru((S)-Tol-BINAP)(O$_2$CCF$_3$)$_2$, and 1 g (7 mmole) of methyl 4-t-butoxy-3-one-butanoate and 50 ml of methanol were added thereto to form a solution. The solution was transferred to a 100 ml-volume autoclave whose atmosphere had been displaced with nitrogen and stirred at 30° C. for 16 hours under a hydrogen pressure of 100 kg/cm$^2$ to conduct hydrogenation. The solvent was removed by distillation, and the residue was distilled under reduced pressure to obtain 649 mg (yield: 65%) of methyl (3R)-4-t-butoxy-3-hydroxybutanoate as a colorless transparent substance.

The methyl (3R)-4-t-butoxy-3-hydroxybutanoate thus obtained was reacted with (R)-(+)-α-methoxy-α-trifluoromethylphenylacetyl chloride in the same manner as in Example 1 to form an ester compound. Analysis by HPLC revealed that the optical purity of methyl (3R)-4-t-butoxy-3-hydroxybutanoate was found to be 96.4 %ee.

EXAMPLE 3

Preparation of Methyl (3S)-4-t-Butoxy-3-hydroxybutanoate

In a 100 ml-volume egg plant type flask equipped with a three-way cock whose atmosphere had been displaced with nitrogen was charged 90 mg (0.106 mmole) of Ru((R)-BINAP)-(O$_2$CCH$_3$)$_2$, and 20 g (106 mmole) of methyl 4-t-butoxy-3-one-butanoate and 60 ml of ethanol were added thereto to form a solution. The solution was transferred to a 100 ml-volume autoclave whose atmosphere had been displaced with nitrogen and stirred at 30° C. for 18 hours under a hydrogen pressure of 100 kg/cm$^2$ to conduct hydrogenation. The solvent was removed by distillation, and the residue was distilled under reduced pressure to obtain 20 g (yield: 95%) of methyl (3S)-4-t-butoxy-3-hydroxybutanoate as a colorless transparent substance.

The methyl (3S)-4-t-butoxy-3-hydroxybutanoate thus obtained was reacted with (R)-(+)-α-methoxy-α-trifluoromethylphenylacetyl chloride in the same manner as in Example 1 to form an ester compound. On analysis by HPLC, the optical purity of methyl (3S)-4-t-butoxy-3-hydroxybutanoate was found to be 90 %ee.

EXAMPLE 4

Preparation of t-Butyl (5S)-6-t-Butoxy-5-hydroxy-3-oxohexanoate

To a three-necked flask equipped with a dropping funnel and a thermometer was charged 80 ml of tetrahydrofuran and cooled to 0° C. in ice-water. To cooled tetrahydrofuran was added 60 ml (60 mmole) of lithium diisopropylamide, and a solution of 6.7 ml (50 mmole) of t-butyl acetate in 15 ml of tetrahydrofuran was added dropwise thereto through the dropping funnel over a period of 30 minutes.

After completion of the dropwise addition, the mixture was stirred for 15 minutes to synthesize a lithium enolate of t-butyl acetate. The reaction mixture was cooled to −50° C. in dry ice-acetone, and a solution of 3.3 g (16.5 mmole) of methyl (3S)-4-t-butoxy-3-hydroxybutanoate as prepared in Example 1 in 15 ml of tetrahydrofuran was added to the mixture through the dropping funnel over 20 minutes, followed by stirred for an additional 1.5 hours. After confirming the completion of the reaction by gas chromatography, 30 ml of a saturated aqueous solution of ammonium chloride and 100 ml of diethyl ether were added to the reaction mixture to conduct extraction. The organic layer was dried over anhydrous magnesium sulfate, and the solvent was removed by distillation. The residue was purified by silica gel column chromatography (diethyl ether/hexane: 1/1 by volume) to obtain 2.3 g (yield: 46%) of t-butyl (5S)-6-t-butoxy-5-hydroxy-3-oxohexanoate.

$^1$H-NMR δ ppm: 1.10 (s, 9H), 1.45 (s, 9H), 2.65 (d, J=6Hz, 2H), 3.35 (d, J=6Hz, 2H), 3.40 (s, 3H), 4.15 (m, 1H)

EXAMPLE 5

Preparation of t-Butyl (3R,5S)-6-t-Butoxy-3,5-dihydroxyhexanoate

In a 100 ml-volume egg plant type flask equipped with a three-way cock whose atmosphere had been displaced with nitrogen was charged 15 mg (0.009 mmole) of Ru$_2$Cl$_4$((R)-BINAP)$_2$(NEt$_3$), and 500 mg (1.75 mmole) of t-butyl (5S)-6-t-butoxy-5-hydroxy-3-oxohexanoate as synthesized in Example 4 and 60 ml of methanol were added thereto to form a solution. The solution was transferred to a 100 ml-volume autoclave whose atmosphere had been displaced with nitrogen and stirred at 30° C. for 16 hours under a hydrogen pressure of 50 kg/cm$^2$ to conduct hydrogenation. The solvent was removed by distillation, and the residue was purified by silica gel column chromatography to obtain 340 mg (yield: 68%) of t-butyl (3R,5S)-6-t-butoxy-3,5-dihydroxyhexanoate.

$^1$H-NMR δ ppm: 1.18 (s, 9H), 1.42 (s, 9H), 1.65 (d, J=6Hz, 2H), 2.35 (d, J=7Hz, 2H), 3.25 (d, J=5Hz, 2H), 4.05 (m, 2H)

The t-butyl (3R,5S)-6-t-butoxy-3,5-dihydroxyhexanoate thus obtained was reacted with acetone dimethyl acetal to synthesize an acetal. The product was found by gas chromatography to comprise 91% of t-butyl (3R,5S)-6-t-butoxy-3,5-dihydroxyhexanoate and 9% of t-butyl (3S,5S)-6-t-butoxy-3,5-dihydroxyhexanoate. Accordingly, the diastereoselectivity of the t-butyl (3R,5S)-6-t-butoxy-3,5-dihydroxyhexanoate was 82 %de.

EXAMPLE 6

Preparation of t-Butyl (3S,5S)-6-t-Butoxy-3,5-dihydroxyhexanoate

In the same manner as in Example 5, 15.8 mg (0.009 mmole) of Ru$_2$Cl$_4$((S)-Tol-BINAP)$_2$(NEt$_3$) was weighed, and 500 mg (1.75 mmole) of t-butyl (5S)-6-t-butoxy-5-hydroxy-3-oxohexanoate as synthesized in Example 4 and 50 ml of methanol were added thereto to form a solution. The resulting solution was transferred to a 100 ml-volume autoclave whose atmosphere had been displaced with nitrogen, and the mixture was stirred at 30° C. for 21 hours under a hydrogen pressure of 50 kg/cm$^2$ to conduct hydrogenation. The solvent was removed by distillation, and the residue was purified by silica gel column chromatography (diethyl ether/hexane: 5/1 by volume) to obtain 345 mg (yield: 70%) of t-butyl (3S,5S)-6-t-butoxy-3,5-dihydroxyhexanoate. The diastereoselectivity of t-butyl (3S,5S)-6-t-butoxy-3,5-dihydroxyhexanoate was determined in the same manner as in Example 5 and found to be 71 %de.

EXAMPLE 7

Preparation of Methyl (3R,5S)-6-t-Butoxy-3,5-dihydroxyhexanoate

Methyl (5S)-6-t-butoxy-5-hydroxy-3-oxohexanoate synthesized in the same manner as in Example 5, except for replacing t-butyl acetate with methyl acetate was used. That is, 16.9 mg (0.01 mmole) of Ru$_2$Cl$_4$((R)-BINAP)$_2$(NEt$_3$) was weighed, and 500 mg (2.15 mmole) of methyl (5S)-6-t-butoxy-5-hydroxy-3-oxohexanoate and 50 ml of methanol were added thereto to form a solution. The solution was transferred to a 100 ml-volume autoclave whose atmosphere had been displaced with nitrogen, and the solution was stirred at 30° C. for 21 hours under a hydrogen pressure of 50 kg/cm$^2$ to conduct hydrogenation. The solvent was removed by distillation, and the residue was purified by silica gel column chromatography (diethyl ether/hexane: 5/1 by volume) to obtain 323 mg (yield: 65%) of methyl (3R,5S)-6-t-butoxy-3,5-dihydroxyhexanoate.

$^1$H-NMR δ ppm: 1.20 (s, 9H), 2.40 (d, J=7Hz, 2H), 3.25 (d, J=5Hz, 2H), 3.70 (s, 3H), 4.10 (m, 2H)

The diastereoselectivity of methyl (3R,5S)-6-t-butoxy-3,5-dihydroxyhexanoate was determined in the same manner as in Example 5 and found to be 65 %de.

EXAMPLE 8

Preparation of t-Butyl (3R,5S)-6-t-Butoxy-3,5-dihydroxyhexanoate

In the same manner as in Example 5, 15 mg (0.009 mmole) of Ru$_2$Cl$_4$((R)-BINAP)$_2$(NEt$_3$) was weighed, and 500 mg (1.75 mmole) of t-butyl (5S)-6-t-butoxy-5-hydroxy-3-oxohexanoate as synthesized in Example 4 and 50 ml of ethanol were added thereto to form a solution. The solution was transferred to a 100 ml-volume autoclave whose atmosphere had been displaced with nitrogen, and the solution was stirred at 30° C. for 16 hours at a hydrogen pressure of 50 kg/cm$^2$ to conduct hydrogenation. The solvent was removed by distillation, and the residue was purified by silica gel column chromatography (diethyl ether/hexane: 5/1 by volume) to obtain 300 mg (yield: 60%) of t-butyl (3R,5S)-6-t-butoxy-3,5-dihydroxyhexanoate.

The diastereoselectivity of the t-butyl (3R,5S)-6-t-butoxy-3,5-dihydroxyhexanoate was determined in the same manner as in Example 5 and found to be 60 %de.

As described above, the present invention provides a process for advantageously obtaining an optically active 6-t-butoxy-3,5-dihydroxyhexanoic ester which is a precursor of a lactone moiety of compactin, mevinolin, or an analogue thereof useful as a cholesterol synthetase inhibitor, which process comprises asymmetric hydrogenation using an optically active ruthenium complex as a catalyst, chain lengthening reaction, and diastereoselective hydrogenation using an optically active ruthenium complex as a catalyst. The process of the invention achieves high enantioselectivity and high diastereoselectivity in hydrogenation which could never been attained by conventional techniques, proving to be an industrially excellent process.

While the invention has been described in detail and with reference to specific embodiments thereof, it will be apparent to one skilled in the art that various changes and modifications can be made therein without departing from the spirit and scope thereof.

What is claimed is:

1. A process for preparing an optically active 6-t-butoxy-3,5-dihydroxyhexanoic ester represented by formula (VII):

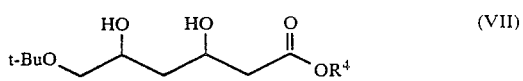

wherein t-Bu represents a t-butyl group; and R$^4$ represents a lower alkyl group, comprising asymmetrically hydrogenating a 4-t-butoxyacetoacetic ester represented by formula (I):

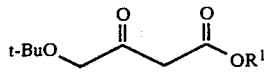  (I)

wherein t-Bu is as defined above; and $R^1$ represents a lower alkyl group, in the presence of a ruthenium-optically active phosphine complex represented by formula (II):

$$Ru(R^2\text{—BINAP})(O_2CR^3)_2 \qquad (II)$$

wherein $R^2$-BINAP represents a tertiary phosphine represented by formula (III):

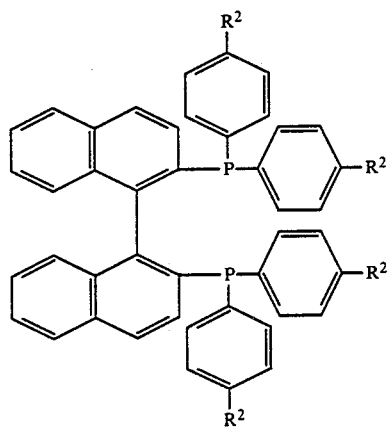  (III)

wherein $R^2$ represents a hydrogen atom or a methyl group; and $R^3$ represents a lower alkyl group or a trifluoromethyl group, to obtain an optically active 4-t-butoxy-3-hydroxybutanoic ester represented by formula (IV):

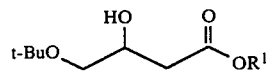  (IV)

wherein t-Bu and $R^1$ are as defined above, reacting the compound represented by formula (IV) with a lithium enolate of an acetic ester to obtain an optically active 6-t-butoxy-5-hydroxy-3-oxohexanoic ester represented by formula (V):

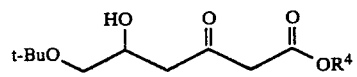  (V)

wherein t-Bu and $R^4$ are as defined above, and then subjecting the compound represented by formula (V) to asymmetric hydrogenation using a ruthenium-optically active phosphine complex represented by formula (VI):

$$Ru_2Cl_4(R^2\text{—BINAP})_2(NEt_3) \qquad (VI)$$

wherein $R^2$-BINAP is as defined above; and Et represents an ethyl group, as a catalyst.

2. A process as in claim 1, wherein in the asymmetric hydrogenation of the 4-t-butoxyacetoacetic ester of formula (I), the ruthenium-optically active phosphine complex of formula (II) is used in an amount of from 0.001 to 0.1 mole per mole of the 4-t-butoxyacetoacetic ester of formula (I).

3. A process as in claim 2, wherein in the asymmetric hydrogenation of the 4-t-butoxyacetoacetic ester of formula (I), the ruthenium-optically active phosphine complex of formula (II) is used in an amount of from 0.002 to 0.01 mole per mole of the 4-t-butoxyacetoacetic ester of formula (I).

4. A process as in claim 1, wherein the asymmetric hydrogenation of the 4-t-butoxyacetoacetic ester of formula (I) is conducted at a temperature of from 25° to 100° C. under a hydrogen pressure of from 5 to 150 kg/cm².

5. A process as in claim 4, wherein the hydrogen pressure is from 30 to 70 kg/cm².

6. A process as in claim 1, wherein the reaction of the optically active 4-t-butoxy-3-hydroxybutanoic ester of formula (IV) is with the lithium enolate of acetic ester and is conducted in tetrahydrofuran at a temperature of −50° C.

7. A process as in claim 1, wherein in the asymmetric hydrogenation of the optically active 6-t-butoxy-5-hydroxy-3-oxohexanoic ester, the ruthenium-optically active phosphine complex of formula (VI) is used in an amount of from 0.001 to 0.1 mole per mole of the optically active 6-t-butoxy-5-hydroxy-3-oxohexanoic ester.

8. A process as in claim 7, wherein in the asymmetric hydrogenation of the optically active 6-t-butoxy-5-hydroxy-3-oxohexanoic ester, the ruthenium-optically active phosphine complex of formula (VI) is used in an amount of from 0.002 to 0.01 mole per mole of the optically active 6-t-butoxy-5-hydroxy-3-oxohexanoic ester.

9. A process as in claim 9, wherein the asymmetric hydrogenation of the optically active 6-t-butoxy-5-hydroxy-3-oxohexanoic ester is conducted at a temperature of from 5° to 100° C. under a hydrogen pressure of from 10 to 120 kg/cm².

10. A process as in claim 9, wherein the asymmetric hydrogenation of the optically active 6-t-butoxy-5-hydroxy-3-oxohexanoic ester is conducted at a temperature of from 30° to 50° C. under a hydrogen pressure of from 50 to 100 kg/cm².

* * * * *